United States Patent
Tanaka et al.

(10) Patent No.: US 10,528,121 B2
(45) Date of Patent: Jan. 7, 2020

(54) SMART WEARABLE DEVICES AND METHODS FOR AUTOMATICALLY CONFIGURING CAPABILITIES WITH BIOLOGY AND ENVIRONMENT CAPTURE SENSORS

(71) Applicants: SONY CORPORATION, Tokyo (JP); SONY CORPORATION OF AMERICA, New York, NY (US)

(72) Inventors: Nobuo Tanaka, Glen Rock, NJ (US); Vladimir Elgort, Staten Island, NY (US); Jacelyn Danielson, San Mateo, CA (US); Anton Kalachev, Burlingame, CA (US); John Wong, Morristown, NJ (US); Behram DaCosta, San Jose, CA (US); Udupi Ramanath Bhat, Mountain View, CA (US); Ludovic Copere, San Jose, CA (US); Masaki Kataoka, Port Washington, NY (US)

(73) Assignees: SONY CORPORATION, Tokyo (JP); SONY CORPORATION OF AMERICA, New York, NY (US)

( * ) Notice: Subject to any disclaimer, the term of this patent is extended or adjusted under 35 U.S.C. 154(b) by 161 days.

(21) Appl. No.: 15/229,382

(22) Filed: Aug. 5, 2016

(65) Prior Publication Data
US 2017/0010664 A1  Jan. 12, 2017

Related U.S. Application Data

(63) Continuation of application No. PCT/US2015/016603, filed on Feb. 19, 2015.
(Continued)

(51) Int. Cl.
*G06F 1/16* (2006.01)
*G06F 3/01* (2006.01)
(Continued)

(52) U.S. Cl.
CPC .............. *G06F 3/011* (2013.01); *G06F 1/163* (2013.01); *G06F 1/1637* (2013.01);
(Continued)

(58) Field of Classification Search
CPC ......... G06F 1/163; G06F 1/1698; G06F 3/014
See application file for complete search history.

(56) References Cited

U.S. PATENT DOCUMENTS

2003/0181795 A1   9/2003   Suzuki et al.
2005/0250996 A1  11/2005   Shirai et al.
(Continued)

FOREIGN PATENT DOCUMENTS

CN    10243806 A      5/2012
JP    20000995456 A   4/2000
(Continued)

OTHER PUBLICATIONS

European Patent Office (EPO), extended European search report dated Oct. 17, 2017, related European application No. EP 15752378.8, pp. 1-10, with claims searched, pp. 11-15.
(Continued)

*Primary Examiner* — Dennis P Joseph
(74) *Attorney, Agent, or Firm* — O'Banion & Ritchey LLP; John P. O'Banion

(57) ABSTRACT

A smart wearable device with sensors that can acquire biological input about the user as well as environmental data is presented. Theses sensors can acquire sensor input which causes the smart wearable device to identify a required task to perform. If the smart wearable device determines that the task can only be performed properly by acquiring new
(Continued)

capabilities, the smart wearable device can automatically acquire the necessary capabilities from various data sources and configure itself to perform the task properly.

7 Claims, 5 Drawing Sheets

Related U.S. Application Data

(60) Provisional application No. 61/943,837, filed on Feb. 24, 2014.

(51) Int. Cl.

| | | |
|---|---|---|
| *G06F 1/3206* | (2019.01) | |
| *G06F 1/3234* | (2019.01) | |
| *G06F 1/3287* | (2019.01) | |
| *G06F 19/00* | (2018.01) | |
| *H04L 29/06* | (2006.01) | |
| *H04W 12/06* | (2009.01) | |
| *G16H 40/63* | (2018.01) | |
| *G16H 40/67* | (2018.01) | |
| *G08B 7/00* | (2006.01) | |

(52) U.S. Cl.
CPC ............ *G06F 1/1698* (2013.01); *G06F 1/325* (2013.01); *G06F 1/3206* (2013.01); *G06F 1/3287* (2013.01); *G06F 3/015* (2013.01); *G06F 3/016* (2013.01); *G06F 19/3418* (2013.01); *G16H 40/63* (2018.01); *G16H 40/67* (2018.01); *H04L 63/0861* (2013.01); *H04L 63/0869* (2013.01); *H04W 12/06* (2013.01); *G06F 1/1626* (2013.01); *G08B 7/00* (2013.01); *Y02D 10/171* (2018.01)

(56) References Cited

U.S. PATENT DOCUMENTS

| | | |
|---|---|---|
| 2007/0055324 A1 | 3/2007 | Thompson et al. |
| 2007/0150589 A1 | 6/2007 | Kim et al. |
| 2007/0161874 A1 | 7/2007 | Aerts |
| 2008/0129621 A1 | 6/2008 | Koshiji |
| 2009/0033622 A1* | 2/2009 | Kalpaxis ................ G06Q 30/06 345/158 |
| 2011/0245633 A1 | 10/2011 | Goldberg et al. |
| 2012/0194419 A1* | 8/2012 | Osterhout .......... G02B 27/0093 345/156 |
| 2012/0212593 A1 | 8/2012 | Naaman |
| 2013/0198694 A1* | 8/2013 | Rahman ................ G06F 3/0484 715/864 |
| 2014/0139422 A1* | 5/2014 | Mistry .................... G06F 3/014 345/156 |
| 2014/0177813 A1* | 6/2014 | Leeds ..................... H04M 3/02 379/67.1 |

FOREIGN PATENT DOCUMENTS

| | | | |
|---|---|---|---|
| JP | 2001-327472 A | 11/2001 | |
| JP | 2007-157165 A | 6/2007 | |
| WO | 2006/059454 A | 6/2006 | |
| WO | 2012170924 A2 | 12/2012 | |
| WO | 2012171032 A2 | 12/2012 | |

OTHER PUBLICATIONS

United States Patent and Trademark Office (USPTO), International Search Report and Written Opinion, PCT International Application No. PCT/US2015/016603, dated Jul. 7, 2015, pp. 1-16, with claims searched, pp. 17-26.

Korean Intellectual Property Office (KIPO), Notice of Preliminary Rejection dated Apr. 19, 2018, Korean-language document pp. 1-6, English-language translation pp. 7-11, English-language claims examined pp. 12-15.

State Intellectual Property Office of the People's Republic of China (SIPO), Notification of the Second Office Action dated Jun. 4, 2018, related Chinese patent application No. 201580007373.4, English-language translation pp. 1-10, claims examined pp. 11-16, Chinese-language document pp. 17-25.

Japan Patent Office (JPO), Notification of Reasons for Refusal dated Jun. 14, 2018, related Japanese patent application No. 2016-551183, Japanese language document pp. 1-4, English-language translation pp. 5-8, claims examined pp. 9-20.

* cited by examiner

SMART WEARABLE DEVICES AND METHODS FOR AUTOMATICALLY CONFIGURING CAPABILITIES WITH BIOLOGY AND ENVIRONMENT CAPTURE SENSORS

CROSS-REFERENCE TO RELATED APPLICATIONS

This application is a 35 U.S.C. § 111(a) continuation of PCT international application number PCT/US2015/016603 filed on Feb. 19, 2015, incorporated herein by reference in its entirety, which claims priority to, and the benefit of, U.S. provisional patent application Ser. No. 61/943,837 filed on Feb. 24, 2014, incorporated herein by reference in its entirety. Priority is claimed to each of the foregoing applications.

The above-referenced PCT international application was published as PCT International Publication No. WO 2015/127067 A1 on Aug. 27, 2015, which publication is incorporated herein by reference in its entirety.

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Field of the Technology

This technology pertains generally to smart wearable devices and more specifically to systems, devices and methods for automatically configuring the smart wearable device in response to automatically identifying the need for new capabilities using a system of non-wearable and wearable sensor and processing devices with location context capture and environment classification.

2. Discussion

Users of smart devices are able to enhance the capabilities and performance of their devices by manually installing new and updated software, applications, etc. However, the user of the device must be aware of the particular software program or application that is needed for enhancing or enabling their device's capabilities or the user must be notified that there is a particular software program or application that is needed for enhancing or enabling their device's capabilities. For devices that are trusted to monitor the health of the user, it is desirable for that device to automatically sense when it needs new capabilities to perform an appropriate task and then automatically acquire what it needs to perform the task properly.

To this end, the location and environmental context of a wearer of a wearable sensor device can be relevant to the function of the sensors of the device and the interpretation of the data that is produced by that device. In addition, the suitability of the associated functions provided by the wearable sensor device and networked wearable and non-wearable devices can also be influenced by the current environment of the wearer. The suitability of device functions and the interpretation of the sensor data produced by the wearable device may change as the environmental context of the wearer changes.

For example, an audible notification from a device could be inaudible in an environment of loud noise or music and therefore ineffective. A light notification could also be lost in an environment of bright sunlight and missed by the user. A heated haptic notification may not be noticed by a hot wearer in an environment that is very hot. Likewise, a loud audio notification may not be appropriate in a quiet environment such as in a library.

Accordingly, there is a need for wearable devices and systems that have programming that can account for the environment of the wearer using sensor control, sensor data interpretation, output control and remote device control so that the smart wearable device can update itself with the appropriate software given its environment and user's needs.

BRIEF SUMMARY

An aspect of this disclosure includes smart wearable devices and methods for automatically configuring capabilities in response to sensor input using sensor data interpretation and device output control that considers the environment of the wearer.

One example embodiment includes a smart wearable device with sensors that can acquire biological input about the user. These sensors may acquire biological sensor input which causes the smart wearable device to identify a required task to perform. If the smart wearable device determines that the task can only be performed properly or more efficiently by acquiring new capabilities, the smart wearable device may automatically acquire the necessary capabilities from various data sources and configure itself to perform the task properly or more efficiently.

Another example embodiment includes a computer implemented method for enabling a smart wearable device to automatically configure itself in response to sensor input. In this embodiment, input may be received from one or more sensors, including the biological sensor or environmental sensor. The context in which the smart wearable device is operating may also be determined automatically. In response to this sensor input, the smart wearable device may match one or more features of the sensor input to any corresponding algorithms readily available to the smart wearable device that are relevant for performing the appropriate task related to the input. In response to an absence of matching features of the sensor input to corresponding algorithms present on the wearable smart device that are relevant for performing the appropriate task, the smart wearable device may automatically request and download a new algorithm (suitable for the appropriate task and the context) from one or more data sources using one or more communications interfaces.

In another embodiment, many types of sensors that can continuously or periodically collect data on the environment surrounding the wearer of a wearable device are utilized. For example, GPS, altitude, air pollution, pollen count, distance traveled, external temperature, decibel level, microphone, video and other sensors can be used alone or in combination to sample the environment. The environment sensor data can be considered within the context of the sensor data obtained from a particular user of a wearable device and the programmed functions of the device.

The interpretation of the sensor data and the resulting outputs of the device in response will benefit from consideration of the context of the sensors and the wearer of the wearable device.

In one embodiment, one or more sensors of the wearable device capture sensor data from the environment surrounding the wearer of the device at regular intervals or samples the environment over time. The acquired sensor data is evaluated and the environment is classified by comparing the captured sensor data with a pre-defined library of environmental sensor data. The responses and functions of the wearable device are then modified based on the sensor data classification. The functions of associated non-wearable or wearable devices can also be modified based on the environment classification through commands through the communications link of the wearable device.

In another embodiment, the wearable device can capture audio information surrounding the wearer and the resulting audio spectrum is transmitted to a remote computer for processing that will be able to match the received information with a library of pre-defined environments (e.g. street, house, forest, face to face conversation, phone conversation, talking with a child, watching a movie, listening to the music, night club etc.). Based on the match, the wearable device can adjust the behavior of itself or other devices such as activating a mute notification, amplifying notifications, enabling other notification means (light, vibration) or determining a social setting to draw a conclusion on user behavior as well as improve sensor function, by selecting or downloading appropriate classification algorithms automatically.

Surrounding sounds and images in an environment can often be used as assistance data to accurately determine a location or social setting. In one embodiment, a wearable device is provided with a microphone that can capture audible information around the wearer and can determine location or social setting more accurately and classify the environment and can use the information to implement necessary behaviors and acquire the necessary software to implement those behaviors.

In another embodiment, a method using audio input on the wearable device to capture environment noise/sounds to improve location context or identify a social setting by comparing a fingerprint of the inputted audio with a database of known audio fingerprints, for example, is also provided.

In yet another embodiment, video images are evaluated to identify subject matter as environment indicators to be used alone or in addition to the library of sensor data classifications and device response programming.

In yet another exemplary embodiment, a system for automatically configuring a smart wearable device in response to sensor input may include data sources that are accessible to smart wearable devices and a smart wearable device capable of obtaining new capabilities from these data sources in response to sensor input. The sensor input may be related to biological characteristics of the user and may also include input related to the user's environment.

Further aspects of the technology will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

DETAILED DESCRIPTION

Figure 1:
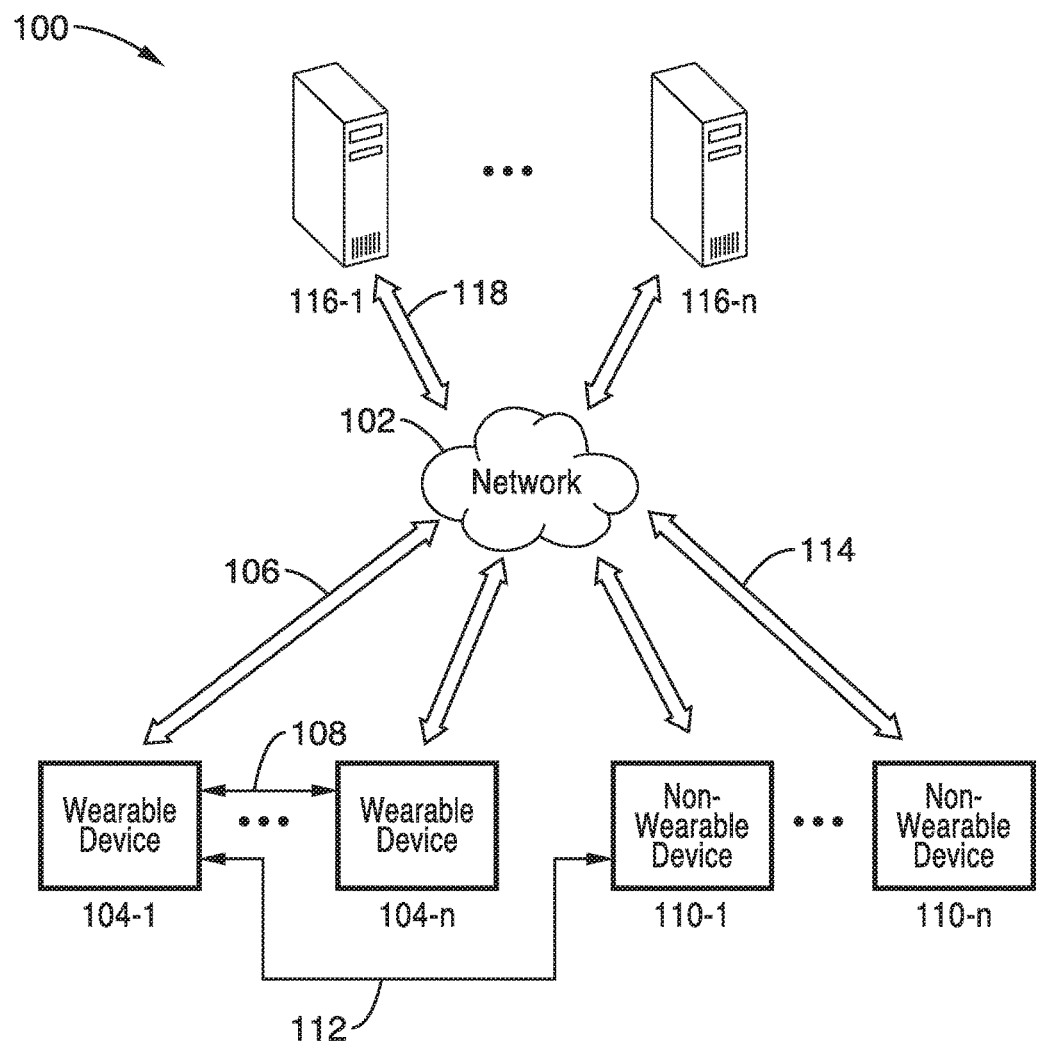
FIG. 1 is a schematic diagram of an embodiment of a smart wearable network described herein.

Referring more specifically to the drawings, for illustrative purposes an embodiment of a wearable apparatus and method for automatically configuring capabilities in response to sensor input using sensor data interpretation and device output control that can consider the biology and environment of the wearer is described and depicted generally in FIG. 1 through FIG. 5. It will be appreciated that the methods may vary as to the specific steps and sequence and the apparatus may vary as to elements and structure without departing from the basic concepts as disclosed herein. The method steps are merely exemplary of the order in which these steps may occur. The steps may occur in any order that is desired, such that it still performs the goals of the claimed technology.

The present disclosure generally pertains to wearable devices that are capable of, for example, performing an action based on one or more biological or physiological characteristics of the user wearing the device. Using one or more sensors, a processor, and code executable on the processor, a wearable device can be configured to sense and process characteristics that include, but are not limited to, a wearer's physical characteristics such as gender, weight, height, body temperature, skin temperature, heart rate, respiration, blood sugar level, blood glucose level, stress/fatigue, galvanic skin response, ingestion (protein), digestion rate, metabolic rate, blood chemistry, sweat, core and skin temperature, vital signs, eye dryness, tooth decay, gum disease, energy storage, calorie burn rate, mental alertness, cardiac rhythm, sleep patterns, caffeine content, vitamin content, hydration, blood oxygen saturation, blood cortisol level, blood pressure, cholesterol, lactic acid level, body fat, protein level, hormone level, muscle mass, pH, etc. Such conditions may also include, but are not limited to, position (e.g., prone, upright), movement, or physical state (e.g., sleeping, exercising), etc.

A wearable device may include one or more output devices that include, but are not limited to, haptic output devices (e.g., offset motors, electroactive polymers, capacitive voltage generators, Peltier temperature elements, contracting materials, Braille coding actuators), telemetry devices, visual devices, audible devices, and other output devices.

A wearable device may include artificial intelligence so that the device can learn and adapt to the wearer. The device may be configured to accurately discriminate between erroneous (accidental, unintended, etc.) and valid sensory inputs, thereby developing accurate conclusions about a wearer's physical state or characteristics (e.g., the device does not interpret a wearer rolling over in their sleep as the wearer exercising). The device may also include one or more cameras or other visual sensors for facial, user, or other image recognition. A wearable device may also be configured to transmit information to and/or retrieve information from a wearer's digital health history.

A wearable device may be configured to output information to a user, to another wearable device, to a non-wearable device, or to a network according to the particular features and function of the device.

A. Generalized System Implementation.

FIG. 1 illustrates a generalized networked infrastructure (e.g., system) 100 that includes a network 102. The network could, for example, be a local area network or a wide area network such as the Internet. One or more smart wearable devices 104-1 through 104-n according to embodiments of the technology described herein may be enabled to communicate with the network 102 through a wired or wireless connection 106. Further, one or more of the smart wearable devices may be enabled to communicate with another smart wearable device through the network 102 or by means of a direct wired or wireless connection 108.

One or more of the smart wearable devices 104-1 through 104-n also may be enabled to communicate with one or more non-wearable devices 110-1 through 110-n. The non-wearable devices, which are beyond the scope of this disclosure, may be any conventional "smart" device with a processor, associated operating system, and communications interface. Examples of non-wearable devices include Smartphones, tablet computers, laptop computers, desktop computers, and set top boxes. Any of the non-wearable devices may be of a type enabled to communicate with an external device through a wired or wireless connection. In that case, one or more of the smart wearable devices may be enabled to communicate with one or more of the non-wearable devices by means of a direct wired or wireless connection 112. Further, one or more of the non-wearable devices may be of a type enabled to communicate with the network 102 through a standard wired or wireless connection 114. In that case, one or more of the smart wearable devices may be enabled to communicate with one or more of the non-wearable devices through the network 102.

One or more servers 116-1 through 116-n may be provided in a client-server configuration and connected to the network by means of a wired or wireless connection 118. The servers may include standalone servers, cluster servers, networked servers, or servers connected in an array to function like a large computer. In that case, one or more of the smart wearable devices may be enabled to communicate with one or more of the servers.

Figure 2:
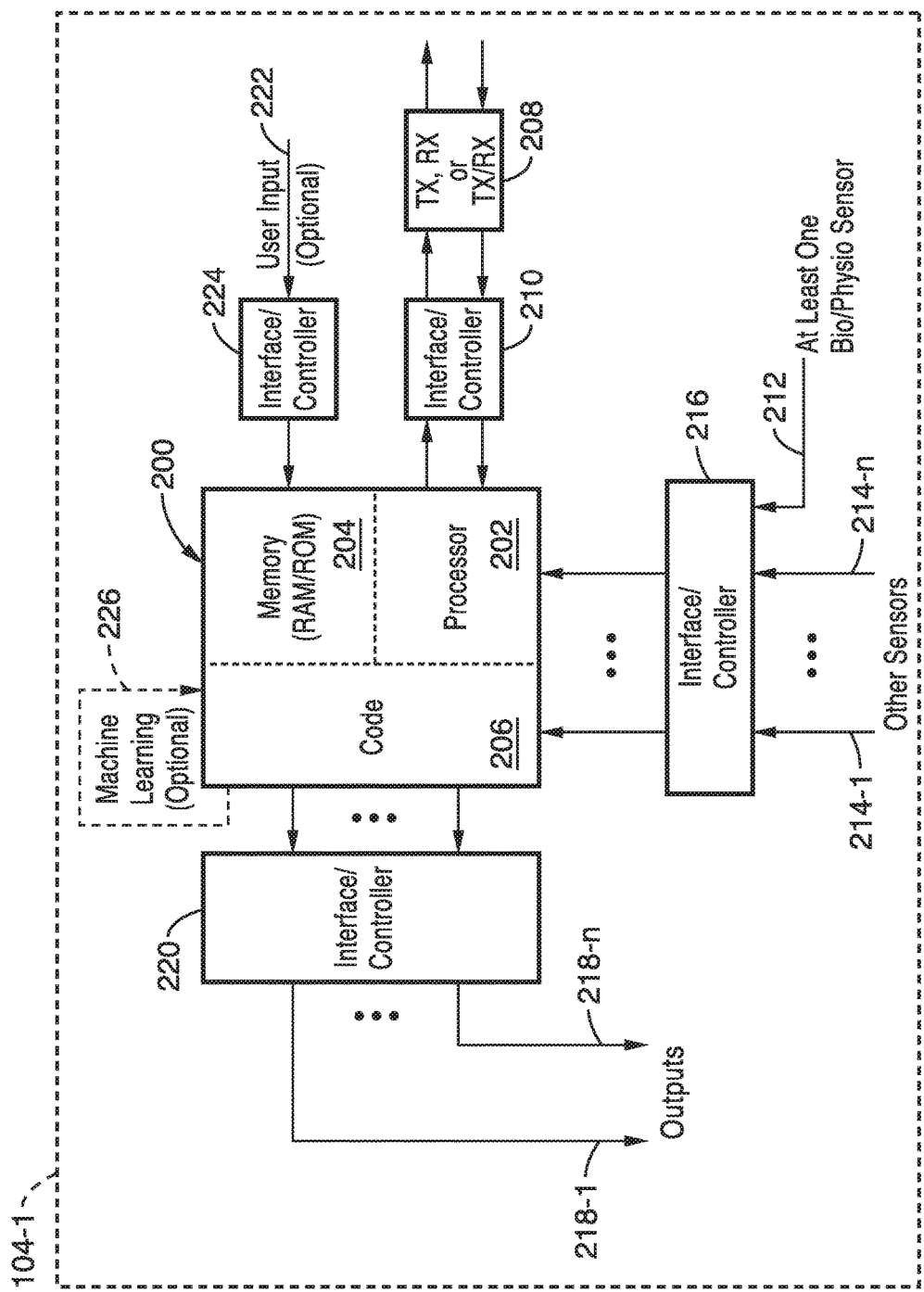
FIG. 2 is a functional block diagram of an embodiment of a smart wearable device described herein.

FIG. 2 illustrates a generalized embodiment of a smart wearable device according to the technology described herein. It will be appreciated that the embodiment shown may be modified or customized to enable performing the functions described herein. In the exemplary embodiment shown, the smart wearable device includes an "engine" 200 having a processor 202, memory 204, and application software code 206. The processor 202 can be any suitable conventional processor. The memory 204 may include any suitable conventional RAM type memory and/or ROM type memory with associated storage space for storing the application programming code 206.

A conventional wired or wireless communications module 208 (e.g., transmitter or receiver or transceiver) may be included as needed for performing one or more of the functions of the smart wearable device described herein. Examples of wireless communication capabilities that can be provided include, but are not limited to, Bluetooth, Wi-Fi, infrared, cellular, and near field communication. One or more conventional interfaces or controllers 210 may also be provided if needed. Examples of interfaces or controllers include, but are not limited to, analog to digital converters, digital to analog converters, buffers, etc.

The device may include at least one input 212 for a biological or physiological sensor for providing input to the device to perform one or more of the functions described herein. Sensor inputs 214-1 through 214-n for optional sensors may be included as well. These optional input sensors may include, but are not limited to, accelerometers, temperature sensors, altitude sensors, motion sensors, position sensors, and other sensors to perform the function(s) described herein. One or more conventional interfaces or controllers 216 may be provided if needed for the sensors. Examples of interfaces or controllers include, but are not limited to, analog to digital converters, digital to analog converters, buffers, etc.

Additionally, the device may include one or more outputs 218-1 through 218-n to drive one or more output devices (and include those output devices). These output devices may include, but are not limited to, haptic output devices, telemetry devices, visual devices, audible devices, and other output devices to perform the functions described herein. One or more conventional interfaces or controllers 220 may be provided if needed for the output devices. Examples of interfaces or controllers include, but are not limited to, analog to digital converters, digital to analog converters, buffers, etc.

A user input 222 may be provided according to the functions described herein. The user input may, for example, initiate one or more functions, terminate one or more functions, or intervene in a running process. The user input can be any conventional input device, including but not limited to, manual switches, touch sensors, magnetic sensors, proximity sensors, etc. One or more conventional interfaces or controllers 224 may be provided if needed for the output devices. Examples of interfaces or controllers include, but are not limited to, analog to digital converters, digital to analog converters, buffers, etc.

Depending on the function(s) described herein, the engine 200 may also include a feedback loop 226 for machine learning or other adaptive functions. The feedback loop may also provide for device calibration.

It will be appreciated that a smart wearable device as described herein would necessarily include a housing or carrier for the above-described components. It will further be appreciated that, as used herein, the term "smart wearable device" means a device that would be worn or otherwise associated with the body of a user and be "connected" to the user by means of at least one sensor for sensing one or more biological or physiological conditions of the user.

The particular form of the housing or carrier (i.e., wearable platform) can vary according to choice and suitability for performing the functions described herein. Examples of wearable platforms include, but are not limited to, hand worn devices, finger worn devices, wrist worn devices, head worn devices, arm worn devices, leg worn devices, angle worn devices, foot worn devices, toe worn devices, watches, eyeglasses, rings, bracelets, necklaces, articles of jewelry, articles of clothing, shoes, hats, contact lenses, gloves, etc.

It will further be appreciated that the input sensors and output devices may be integrated into the wearable platform, or may be external to the wearable platform, as is desired and/or suitable for the function(s) of the smart wearable device.

B. Smart Wearable Device to Automatically Configure Itself in Response to Sensor Input Such as Environmental Capture.

Figure 3:
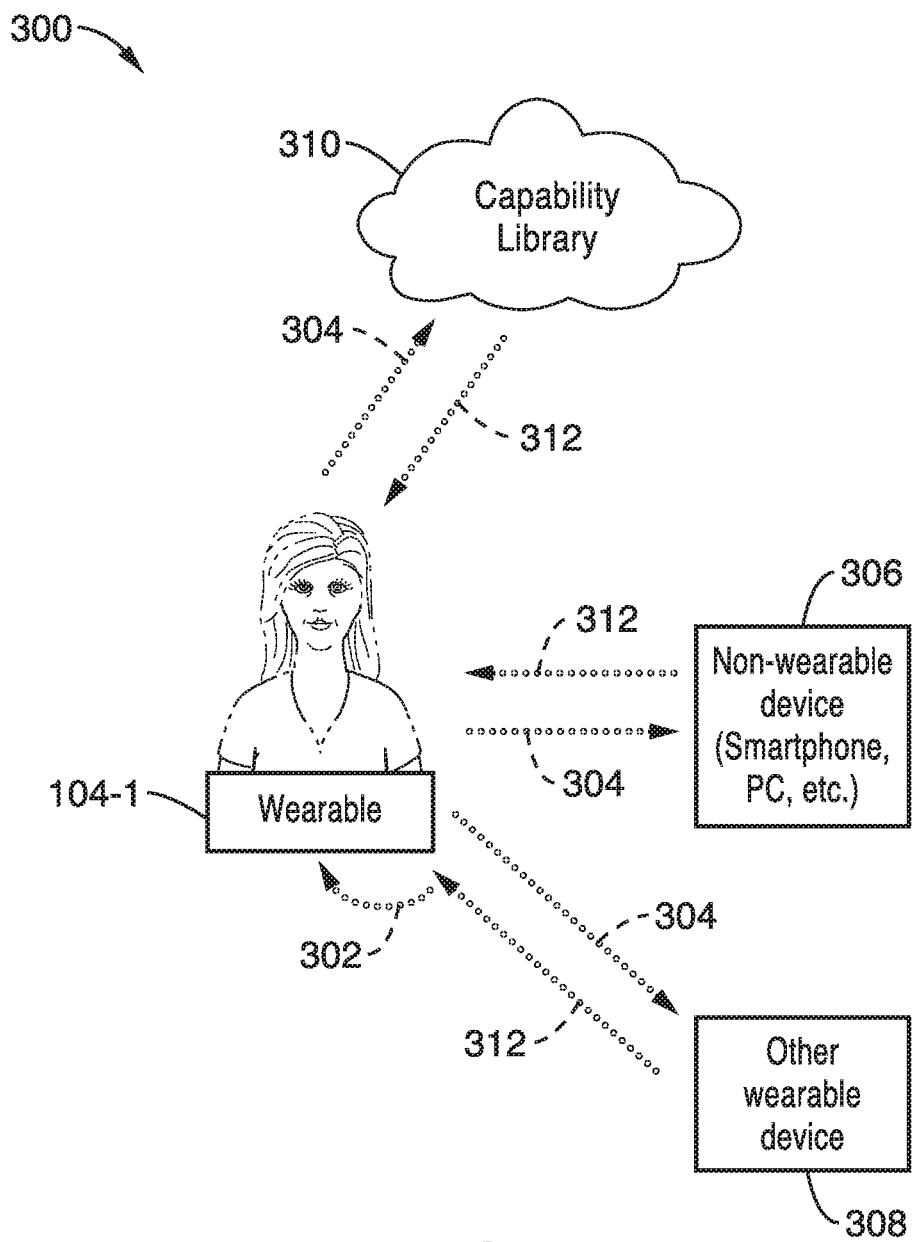
FIG. 3 is a schematic diagram of the smart wearable device and system for detecting the need for new capabilities and requesting the new capabilities from multiple data sources.

Referring now to FIG. 3, a schematic diagram 300 is shown illustrating a system and a smart wearable device 104-1 that includes one or more sensors 214-1, 214-n, 420-470 (see FIG. 2 and FIG. 4), with at least one of these sensors being a biological sensor 212 configured to acquire biological sensor input about the user. Examples of biological sensor input related to one or more of the user's biological characteristics includes blood sugar, stress, fatigue, anxiety, alertness, heart rate, galvanic skin response, weight, nutrition, digestion rate, metabolic rate, body temperature, skin temperature, respiration, allergies, sleep patterns, hydration, drug levels, sweat production and blood analysis. It should be noted that this list of examples is in no way limiting.

The smart wearable device 104-1 shown in this embodiment may, for example, receive sensor input 302 from the biological sensor 212. In response to receiving the sensor input 302, the smart wearable device 104-1 may automatically identify an appropriate task related to the received input. Accordingly, the smart wearable device can match features of the sensor input to any corresponding algorithms (capabilities) readily available to the wearable smart device 104-1 that are relevant for performing the appropriate task. If the smart wearable device 104-1 cannot match features of the sensor input to corresponding algorithms present on the wearable smart device 104-1, the smart wearable device may automatically request a new algorithm 304 from several data sources. By way of example and not limitation, the data sources may include non-wearable devices 306 such as tablets and smartphones, other wearable devices 308 and storage systems 310, such as cloud storage. The smart wearable device 104-1 may automatically download 312 the new algorithm to perform the appropriate task that corresponds to the received sensor input 302.

An embodiment of a wearable device according to this disclosure may have at least one sensor that acquires contextual data from the environment surrounding the wearer of the wearable device. The device may store the acquired data in memory for processing with a processor within the device or the data may be transmitted through an optional communications link to a remote computer for processing or to cloud storage. The wearable apparatus also has a number of output devices and control capabilities.

Figure 4:
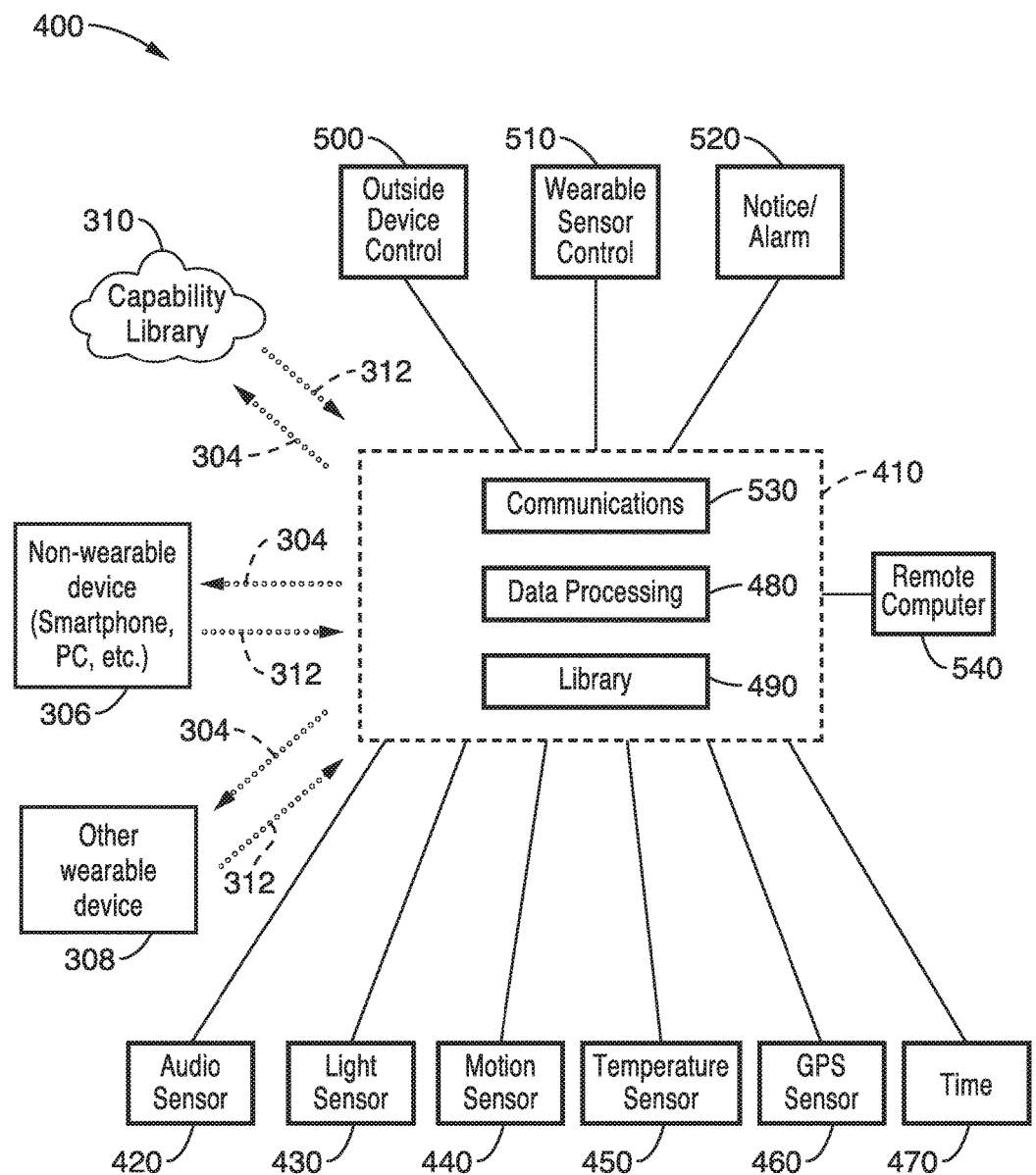
FIG. 4 is a functional block diagram of another configuration an embodiment of a smart wearable device described herein.

Referring now to FIG. 4, one configuration of a wearable device 400 is functionally shown in detail. The wearable device has one or more sensors that are connected with a processing module 410 for sensor data processing and storage. In the embodiment illustrated in FIG. 4, the array of sensors includes an audio sensor 420, a light or video sensor 430, a motion sensor 440, a temperature sensor 450, a GPS location sensor 460 and a clock 470. Although these environmental sensors are shown as examples, other sensors can be used to sense the environmental conditions of the wearable device. In other embodiments, at least one sensor acquiring biological or physical data from a wearer of the wearable device may also be included in the array of sensors.

The processing module 410 can have a sensor data processing function 480 with programming that collects sensor data from one or more of the sensors and compares the sensor data with a library 490 of classified sensor data for each type of sensor to give a classification to the acquired data. The programming may also include output commands or instructions for each classification or group of classifications relating to outside device control 500, wearable sensor control 510 and a notification or alarm 520 or other functions provided by the particular wearable sensor device configuration.

The classification of sensor data by the data processing 480 programming can also be performed remotely through the communications link 530. In one embodiment, the raw or processed data from one or more sensors is transmitted to a remote computer 540 or other non-wearable 500 device for classification. The library of sensor classifications may be located on the remote computer 540 and the data processing 480 on the wearable device stores and transfers the data. The communications link 530 may also provide an interface to communicate programming commands between the remote computer and the wearable device that can control the functions of the components of both. Several wearable devices can also be part of a network of devices with one remote computer 540.

The apparatus can also communicate data processed at the processor 480 or remote computer 540 to another device 500 over a communication network (e.g. LAN such as Bluetooth, WiFi and/or WAN such as internet or a cellular network). For example, the processor 480 can communicate with other outside devices 500 such as a cell phone over the communications link 530 and can send and receive control commands with the outside device 500 including commands based on the classification of sensor data from the wearable device.

The programming at the processor 480 can also control the sensors 510 of the wearable sensor device in the event of the occurrence of certain environmental classifications. Some sensors can be activated or turned off for a period of time depending on the current environment and sensor data classifications.

The programming at processor 480 may also provide a notice or alarm function using one or more haptic devices and non-haptic devices that can notify the wearer of the wearable sensor device of the occurrence of a variety of events. For example, the alarm may actuate when the classifications cause a change in a function of the wearable device. A notification in the form of a vibration at a particular frequency could also occur when a communication with an outside device occurs, when the wearable device has automatically updated its software or when the external temperature of the environment exceeds a selected high or low.

The environmental classification of sensor data can also include additional input from audio or video data analysis. Analysis of background sounds can often be used to assist in the accurate determination of the location or social setting of the wearable device. For example, in one embodiment, the audio sensor 420 output is evaluated with voice or word recognition programming. The meaning of recognized words is used in conjunction with the other sensor data to accurately establish the location or setting. For example, words related to food or eating could be used to suggest a dining or restaurant setting and updates to maps and restaurant listings can be made automatically.

In another embodiment, video data from a video camera could be evaluated with face recognition or other subject matter identification programming to assist in the accurate determination of the environment or setting of the wearer of the wearable device. The presence and number of faces can assist in the accurate determination of setting or location of the wearable device.

In yet another embodiment, the wearable device may detect a low light environment and can dim its display as a result of programming determining that increasing the brightness of the display to make the information legible will not be worth the increased power drain. Consequently, a subset of displayed information may be switched to audible or haptic feedback. An example of how this can work is where information about the wearer's pulse is communicated aurally or through haptic notification. Although communicating a wearer's actual heart rate by haptic feedback may be overwhelming (e.g. 140 beats per minute in haptic feedback or a tone sounding 140 times in one minutes), the wearable device can be programmed to determine which of two or three bands the wearer's pulse rate fits within and generate a tone or haptic response specific to that particular band. An example of the pulse bands could be: <100 beats/min; 100-120 beats/min; 130-140 beats/min; >140 beats/min. The low light environment could be determined by the programming based on the user inputting that they are running or inputting a running workout or by detecting the time of day.

In yet another embodiment, the wearable device can be synchronized with another device (phone or cloud server) and can access the wearer's calendar. If the wearable detects an event such as a race, the wearable can then change its running program or training program to coincide with the remaining days until the race to improve performance. The user's fitness and speed can be increased in subsequent runs as the wearable device's programming gradually modifies the interval profiles to increase intensity (pace, duration of a high intensity interval, etc.). For example, pace information is communicated haptically or aurally to the user during the run (more beats could indicates a faster pace).

The smart wearable device 400 shown in this embodiment can receive sensor input from one or more environmental sensors 420, 430, 440, 450, 460 and 470. In response to receiving the sensor input, the smart wearable device may automatically identify an appropriate task related to the received input. Accordingly, the smart wearable device 400 may match features of the sensor input to any corresponding algorithms (capabilities) readily available to the wearable smart device 400 that are relevant for performing the appropriate task. If the smart wearable device 400 cannot match features of the sensor input to corresponding algorithms present on the wearable smart device 400, the smart wearable device may automatically request a new algorithm 304 from several data sources. By way of example and not limitation, the data sources may include non-wearable devices 306 such as tablets and smartphones, other wearable devices 308 and storage systems 310, such as cloud storage. The smart wearable device 400 may automatically download 312 the new algorithm to perform the appropriate task that corresponds to the received sensor input.

Accordingly, the programming described in FIG. 4 enables a wearable device to automatically generate appropriate responses by a wearable sensor device and associated non-wearable devices that account for the biological status of the wearer or current environment of the wearable device without any intervention by the wearer.

Figure 5:
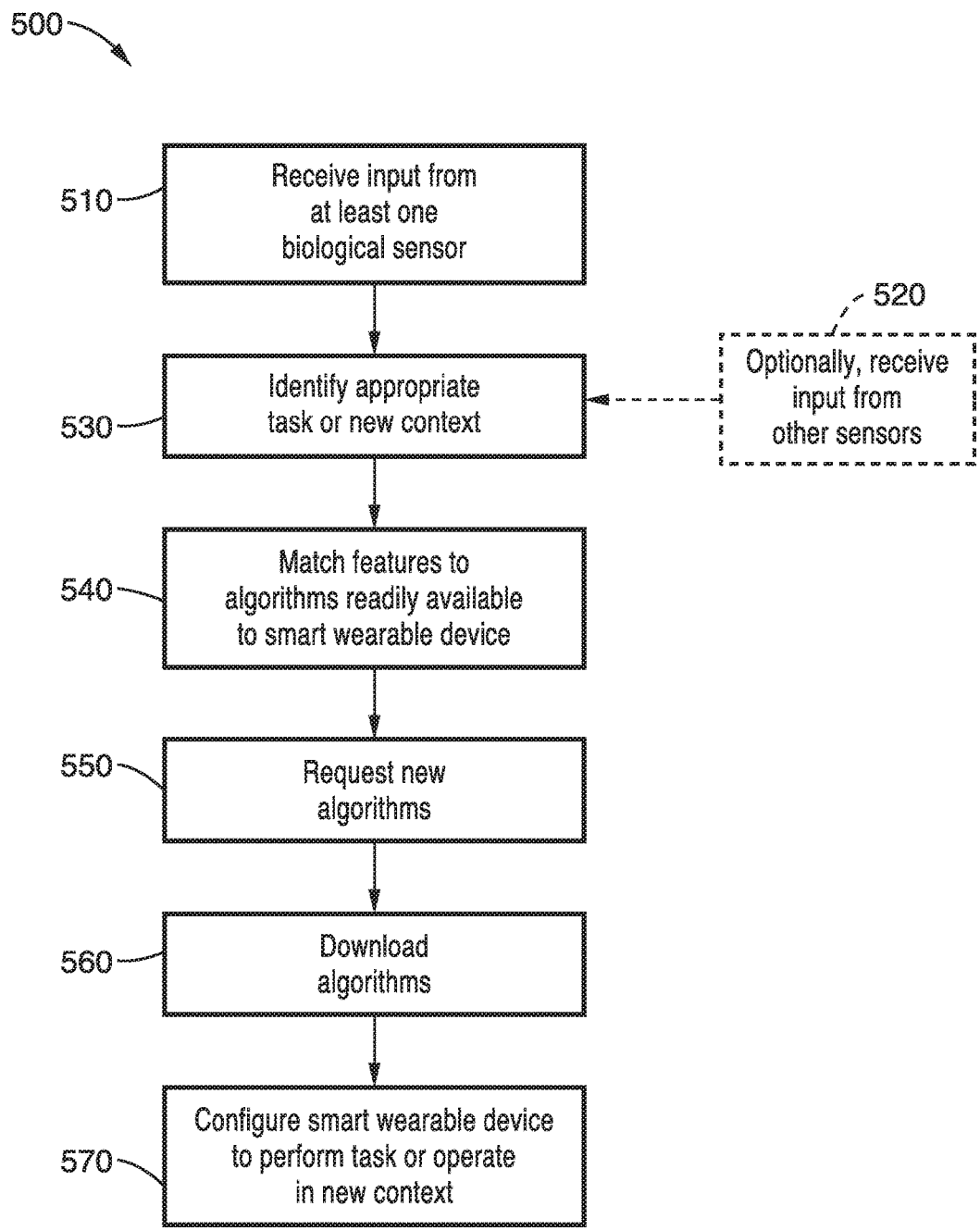
FIG. 5 is a flow diagram illustrating the method for detecting the need for new capabilities and requesting the new capabilities from multiple data sources.

FIG. 5 is a flow diagram 500 of a method for automatically configuring a smart wearable device using sensor algorithms (capabilities) downloaded from other devices and data storage systems in response to automatically determining that an appropriate task should be performed given a user's signals, such as biological or physiological signals or a new context that the device is now operating in. In the example embodiment shown in FIG. 5, a smart wearable device may receive input from at least one biological sensor located in or external to the smart wearable device 510. The smart wearable device may also optionally receive input from other sensors such as environmental sensors 520. Using this input, the smart wearable device may then automatically identify an appropriate task to perform or a new context in which the device is operating 530. An example of a new context may be an awake user (one context) that has gone to sleep (new context). Another example of a new context may be when the smart wearable device receives changes in biological input from the user such as patterns of sleep, heart rate and skin temperature. These changes may cause the smart wearable device to predict that the user could have a specific medical condition and then automatically request and download new algorithms to fine tune its own algorithms to monitor the user's vital signs much closer and adjust outputs necessary for the new context.

The smart wearable device may then match the features of the sensor input to any corresponding algorithms that are relevant for performing the appropriate task or operating in the new context that are readily available to the smart wearable device (i.e. present on the smart wearable device) 540. In response to an absence of matching features to algorithms that are relevant for performing the appropriate task or operating in the new context that are readily available to the smart wearable device, the smart wearable device may request a new algorithm from one or more data sources 550. The smart wearable device can automatically determine whether the new algorithm from the other data sources is suitable for the new task and/or new context. The new algorithm may be automatically downloaded by the smart wearable device 560 which can enable the smart wearable device to automatically configure itself 570 to perform the new task and operate in the new context.

CONCLUSION

The number of sensors on a smart wearable device may be finite but the sensor fusion algorithms leverage these sensors and create value that is much greater than that which is present on the device. Furthermore, since the smart wearable device described herein has the capability to sense a user's physical, biological and environmental condition, it is desirable that the device should also be able to intelligently search for capabilities that it needs in a new context.

Embodiments of the present technology may be described with reference to flowchart illustrations of methods and systems according to embodiments of the technology, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula (e), or computational depiction(s).

It will further be appreciated that "programming" as used herein refers to one or more instructions that can be executed by a processor to perform a function as described herein. The programming can be embodied in software, in firmware, or in a combination of software and firmware. The programming can be stored local to the device in non-transitory media, or can be stored remotely such as on a server, or all or a portion of the programming can be stored locally and remotely. Programming stored remotely can be downloaded (pushed) to the device by user initiation, or automatically based on one or more factors, such as, for example, location, a timing event, detection of an object, detection of a facial expression, detection of location, detection of a change in location, or other factors. It will further be appreciated that as used herein, that the terms processor, central processing unit (CPU), and computer are used synonymously to denote a device capable of executing the programming and communication with input/output interfaces and/or peripheral devices.

From the discussion above it will be appreciated that the technology can be embodied in various ways, including but not limited to the following:

1. A smart wearable device, the device comprising: (a) a housing, wherein the housing encases components of a wearable smart device; (b) one or more sensors, wherein at least one sensor is a biological sensor configured to acquire biological input; (c) a memory; (d) one or more communications interfaces; (e) a processor; and (f) programming residing in a non-transitory computer readable medium, wherein the programming is executable by the computer processor and configured to: (i) receive input from the one or more sensors to automatically identify an appropriate task related to the input and a context in which said device is operating; (ii) match features of the sensor input to any corresponding algorithms readily available to the wearable smart device that are relevant for performing the required task; (iii) in response to an absence of matching features of the sensor input to corresponding algorithms present on the wearable smart device that are relevant for performing the required task or operating in the new context, automatically request a new algorithm from one or more data sources via the one or more communications interfaces, wherein the new algorithm is suitable for the appropriate task and the new context; and (iii) automatically download the new algorithm to the smart wearable device to perform the appropriate task or operate in the new context.

2. The device as recited in any previous embodiment, wherein the one or more data sources are selected from the group of data sources consisting of a cloud storage system, a non-wearable device and another wearable device.

3. The device as recited in any previous embodiment, wherein at least one sensor is an environmental sensor configured to acquire input about the device's environment.

4. The device as recited in any previous embodiment, wherein the smart wearable device has a platform selected from the group consisting of hand worn devices, finger worn devices, wrist worn devices, head worn devices, arm worn devices, leg worn devices, angle worn devices, foot worn devices, toe worn devices, watches, eyeglasses, rings, bracelets, necklaces, articles of jewelry, articles of clothing, shoes, hats, contact lenses, and gloves.

5. The device of as recited in any previous embodiment, wherein the one or more communications interfaces are selected from the group consisting of a wired communications interface, a wireless communications interface, a cellular communications interface, a WiFi communications interface, a near field communications interface, an infrared communications interface, and a Bluetooth communications interface.

6. The device as recited in any previous embodiment, wherein a user of the smart wearable device can manually download the new algorithm to the smart wearable device for performing required tasks.

7. The device as recited in any previous embodiment, wherein the sensor input is related to one or more of the user's biological characteristics consisting of blood sugar, stress, fatigue, anxiety, alertness, heart rate, galvanic skin response, weight, nutrition, digestion rate, metabolic rate, body temperature, skin temperature, respiration, allergies, sleep patterns, hydration, drug levels, sweat production and blood analysis.

8. A computer implemented method for enabling a smart wearable device to automatically configure itself in response to sensor input, the method comprising: (a) providing a smart wearable device, the device comprising: (i) a housing, wherein the housing encases components of a wearable smart device; (ii) one or more sensors, wherein at least one sensor is a biological sensor configured to acquire biological input; (iii) a memory; (iv) one or more communications interfaces; and (v) a processor; (b) receiving input from one or more sensors to automatically identify an appropriate task related to the input and a context in which a smart wearable device is operating, wherein at least one or more sensors is a biological sensor configured to acquire biological input; (c) matching one or more features of the sensor input to any corresponding algorithms readily available to the wearable smart device that are relevant for performing the appropriate task related to the input and context in which a smart wearable device is operating; (d) in response to an absence of matching features of the sensor input to corresponding algorithms present on the wearable smart device that are relevant for performing the required task, automatically requesting a new algorithm from one or more data sources via the one or more communications interfaces, wherein the new algorithm is suitable for the appropriate task related to the input and context in which a smart wearable device is operating; and (e) automatically downloading the new algorithm to the smart wearable device to perform the appropriate task related to the input and operate in the identified context in which a smart wearable device is operating; (f) wherein said method is performed by executing programming on at least one computer processor, said programming residing on a non-transitory medium readable by the computer processor.

9. The method as recited in any previous embodiment, wherein the one or more data sources are selected from the group of data sources consisting of a cloud storage system, a non-wearable device and another wearable device.

10. The method as recited in any previous embodiment, wherein the smart wearable device has a platform selected from the group consisting of hand worn devices, finger worn devices, wrist worn devices, head worn devices, arm worn devices, leg worn devices, angle worn devices, foot worn devices, toe worn devices, watches, eyeglasses, rings, bracelets, necklaces, articles of jewelry, articles of clothing, shoes, hats, contact lenses, and gloves.

11. The method as recited in any previous embodiment, wherein the one or more communications interfaces are selected from the group consisting of a wired communications interface, a wireless communications interface, a cellular communications interface, a WiFi communications interface, a near field communications interface, an infrared communications interface, and a Bluetooth communications interface.

12. The method as recited in any previous embodiment, wherein a user of the smart wearable device can manually download the new algorithm to the smart wearable device for performing the appropriate task related to the input and operating in the identified context.

13. The method as recited in any previous embodiment, wherein the sensor input is related to one or more of the user's biological characteristics consisting of blood sugar, stress, fatigue, anxiety, alertness, heart rate, galvanic skin response, weight, nutrition, digestion rate, metabolic rate, body temperature, skin temperature, respiration, allergies, sleep patterns, hydration, drug levels, sweat production and blood analysis.

14. The method as recited in any previous embodiment, wherein at least one sensor is an environmental sensor configured to acquire input about the device's environment.

15. A system for automatically configuring a smart wearable device in response to sensor input, the system comprising: (a) one or more data sources; and (b) a wearable smart device comprising: (i) a housing, wherein the housing encases components of a wearable smart device; (ii) one or more sensors, wherein at least one sensor is a biological sensor configured to acquire biological input; (iii) a memory; (iv) one or more communications interfaces; (v) a processor; and (vi) programming residing in a non-transitory computer readable medium, wherein the programming is executable by the computer processor and configured to: receive input from the one or more sensors to automatically identify an appropriate task related to the input and a context in which said device is operating; match features of the sensor input to any corresponding algorithms readily available to the wearable smart device that are relevant for performing the required task; in response to an absence of matching features of the sensor input to corresponding algorithms present on the wearable smart device that are relevant for performing the required task or operating in the new context, automatically request a new algorithm from one or more data sources via the one or more communications interfaces, wherein the new algorithm is suitable for the appropriate task and the new context; and automatically download the new algorithm to the smart wearable device to perform the appropriate task or operate in the new context.

16. The system as recited in any previous embodiment, wherein the one or more data sources are selected from the group of data sources consisting of a cloud storage system, a non-wearable device and another wearable device.

17. The system as recited in any previous embodiment, wherein the smart wearable device has a platform selected from the group consisting of hand worn devices, finger worn devices, wrist worn devices, head worn devices, arm worn devices, leg worn devices, angle worn devices, foot worn devices, toe worn devices, watches, eyeglasses, rings, bracelets, necklaces, articles of jewelry, articles of clothing, shoes, hats, contact lenses, and gloves.

18. The system as recited in any previous embodiment, wherein the one or more communications interfaces are selected from the group consisting of a wired communications interface, a wireless communications interface, a cellular communications interface, a WiFi communications interface, a near field communications interface, an infrared communications interface, and a Bluetooth communications interface.

19. The system as recited in any previous embodiment, wherein a user of the smart wearable device can manually download the new algorithm to the smart wearable device for performing required tasks.

20. The system as recited in any previous embodiment, wherein the sensor input is related to one or more of the user's biological characteristics consisting of blood sugar, stress, fatigue, anxiety, alertness, heart rate, galvanic skin response, weight, nutrition, digestion rate, metabolic rate, body temperature, skin temperature, respiration, allergies, sleep patterns, hydration, drug levels, sweat production and blood analysis.

21. A wearable sensor apparatus with environmental capture, comprising: (a) a computer processor with memory; (b) a plurality of sensors operably coupled to the processor; (c) a library of pre-defined environmental sensor data for a plurality of sensors; and (d) programming in a non-transitory computer readable medium and executable on the computer processor for performing steps comprising: (i) capturing sensor data at regular intervals over time; (ii) classifying the captured sensor data by comparing the captured sensor data with the pre-defined library of environmental sensor data; and (iii) modifying wearable device functions based on the sensor data classification.

22. An apparatus as recited in any previous embodiment, wherein the sensor is a sensor selected from the group of sensors consisting of a sound sensor, a light sensor, a temperature sensor, an altitude sensor, a motion sensor, a video sensor, and a position sensor.

23. An apparatus as recited in any previous embodiment, wherein the programming further comprises the steps: evaluating captured sound sensor data to detect words; and using the meaning of detected words in the classification of the current environment.

24. An apparatus as recited in any previous embodiment, wherein the programming further comprises the steps: evaluating captured video camera sensor data to detect the presence of faces; and using the presence of detected faces in the classification of the current environment.

25. An apparatus as recited in any previous embodiment, the wearable apparatus further comprising: a notification output device coupled to the processor configured to notify the wearer of the wearable apparatus of modification events.

26. An apparatus as recited in any previous embodiment, wherein the notification output device comprises a haptic device selected from the group of haptic devices consisting of a vibrating device, a heating element, a cooling element, an electroactive polymer, a capacitive voltage generator, and a Braille coding actuator.

27. An apparatus as recited in any previous embodiment, wherein the notification output device comprises a non-haptic device selected from the group of non-haptic devices consisting of a light generating device and a sound generating device.

28. An apparatus as recited in any previous embodiment, the wearable apparatus further comprising: (a) a communications link operably coupled to the processor, the link having a transmitter and receiver; and (b) programming in a non-transitory computer readable medium and executable on the computer processor for performing steps comprising: (i) transmitting acquired sensor data to a remote computer; (ii) receiving environment classifications and program commands from the remote computer; and (iii) executing program commands received from the remote computer.

29. An apparatus as recited in any previous embodiment, wherein the remote computer comprises a non-wearable device.

30. An apparatus as recited in any previous embodiment, wherein the communication between the wearable device and the remote computer is a wireless communication system selected from the group of systems consisting of Bluetooth, Wi-Fi, infrared, cellular, and near field communications.

31. A computer implemented method for monitoring wearable sensors and location context, the method comprising: (a) providing a library of pre-defined environmental sensor data for different types of sensors; (b) capturing sensor data from sensors of a wearable sensor device over time; (c) classifying the captured sensor data by comparing the captured sensor data with the pre-defined library of environmental sensor data; and (d) modifying wearable device functions based on the sensor data classification; (e) wherein the method is performed by executing programming on at least one computer processor, the programming residing on a non-transitory medium readable by the computer processor.

32. A method as recited in any previous embodiment, further comprising: actuating a notification output device to notify the wearer of the wearable apparatus of function modification events.

33. A method as recited in any previous embodiment, further comprising: capturing sound sensor data; evaluating captured sound sensor data to detect words; and using the meaning of detected words in the classification of the current environment sensor data.

34. A method as recited in any previous embodiment, further comprising: capturing video camera sensor data; evaluating captured video camera sensor data to detect the presence of faces; and using the presence of detected faces in the classification of the current environment sensor data.

35. A method as recited in any previous embodiment, further comprising: communicating acquired sensor data to a remote computer through a communications link; receiving program commands for the wearable device from the remote computer; and executing program commands received from the remote computer.

36. A method as recited in any previous embodiment, further comprising: designating program commands for control of remote computer functions based on acquired sensor data classifications; and transmitting program commands to a remote computer from the wearable device through a communications link; wherein control of designated remote computer functions is initiated by wearable sensor data classification.

Although the description above contains many details, these should not be construed as limiting the scope of the technology but as merely providing illustrations of some of the presently preferred embodiments of this technology. Therefore, it will be appreciated that the scope of the present technology fully encompasses other embodiments which may become obvious to those skilled in the art, and that the scope of the present technology is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present technology, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112 unless the element is expressly recited using the phrase "means for" or "step for".

What is claimed is:

1. A smart wearable device, the device comprising:
   (a) a housing, wherein the housing encases components of a wearable smart device;
   (b) one or more sensors, wherein at least one sensor is a biological sensor configured to acquire biological input of a wearer;
   (c) a memory;
   (d) one or more communications interfaces;
   (e) a processor; and
   (f) programming residing in a non-transitory computer readable medium, wherein the programming is executable by the computer processor and configured to:
      (i) receive biological input from the one or more sensors to automatically identify an appropriate task to process the biological input and a context in which said device is operating, the context being derived from contextual data received from the one or more sensors relating to the biological input and an environment surrounding the wearer;
      (ii) match features of the sensor input to one or more corresponding algorithms readily available to the wearable smart device that are relevant for performing the task and operating in the context;
      (iii) in response to finding an absence of matching features of the sensor input to corresponding algorithms present on the wearable smart device that are relevant for performing the task and operating in the context, match the features of the sensor input to one or more algorithms within a plurality of algorithms being stored in one or more external data sources and automatically request a new algorithm from the one or more data sources via the one or more communications interfaces, wherein the new algorithm is suitable for execution on the wearable device to perform the task and operate on the matched sensor input in the context; and (iv) automatically download the new algorithm to the smart wearable device to perform the appropriate task and operate in the context, said matching and download occurring without user input or selection.

2. The device of claim 1, wherein the one or more data sources are selected from the group of data sources consisting of a cloud storage system, a non-wearable device and another wearable device.

3. The device of claim 1, further comprising: an environmental sensor configured to acquire the contextual data about the device's environment.

4. The device of claim 1, wherein the smart wearable device has a platform selected from the group consisting of hand worn devices, finger worn devices, wrist worn devices, head worn devices, arm worn devices, leg worn devices, angle worn devices, foot worn devices, toe worn devices, watches, eyeglasses, rings, bracelets, necklaces, articles of jewelry, articles of clothing, shoes, hats, contact lenses, and gloves.

5. The device of claim 1, wherein the one or more communications interfaces are selected from the group consisting of a wired communications interface, a wireless communications interface, a cellular communications interface, a WiFi communications interface, a near field communications interface, an infrared communications interface, and a Bluetooth communications interface.

6. The device of claim 1, wherein said programming is further configured for allowing a user of the smart wearable device to manually download the new algorithm to the smart wearable device for performing required tasks.

7. The device of claim 1, wherein the sensor input is related to one or more of the user's biological characteristics consisting of blood sugar, stress, fatigue, anxiety, alertness, heart rate, galvanic skin response, weight, nutrition, digestion rate, metabolic rate, body temperature, skin temperature, respiration, allergies, sleep patterns, hydration, drug levels, sweat production and blood analysis.

* * * * *